United States Patent [19]

Barda et al.

[11] Patent Number: 5,266,295
[45] Date of Patent: Nov. 30, 1993

[54] HYDROGEN PEROXIDE OXIDATION OF BROMIDE TO BROMIDE

[75] Inventors: Henry J. Barda, Brunswick, N.J.;

[73] Assignee: Akzo American Inc., Chicago, Ill.

[21] Appl. No.: 982,040

[22] Filed: Nov. 24, 1992

Related U.S. Application Data

[63] Continuation of Ser. No. 474,706, Jan. 30, 1990, abandoned, which is a continuation of Ser. No. 343,713, Apr. 27, 1989, abandoned.

[51] Int. Cl.$^5$ ............................................. C01B 7/07
[52] U.S. Cl. ................................. 423/500; 423/502; 423/507
[58] Field of Search ..................... 423/500, 502, 507

[56] References Cited

U.S. PATENT DOCUMENTS

| | | | |
|---|---|---|---|
| 3,959,450 | 5/1976 | Calloue et al. | 423/507 |
| 4,029,732 | 6/1977 | Callove et al. | 423/500 |
| 4,214,103 | 7/1980 | Garman | 568/639 |
| 4,387,253 | 6/1983 | Gower | 568/812 |
| 4,447,405 | 5/1984 | Ahn et al. | 423/88 |
| 4,450,291 | 5/1984 | Chi et al. | 562/530 |

FOREIGN PATENT DOCUMENTS 2713345 3/1977 Fed. Rep. of Germany .

OTHER PUBLICATIONS

Chemical Abstracts #90:57290g 1979.
Chemical Abstracts #90:151811z 1979.
Chemical Abstracts #93:185950w.
Chemical Abstracts #106:32598z.
Bailar, I. C. ed, "Comprehensive Inorganic Chemistry", vol. 2 Pergammon Press; 1973 pp. 1136–1138 and 1192.
P. Schubert et al. "Recover Bromine on Site" Chemtech Apr. 1993 pp. 37–41.

*Primary Examiner*—John Niebling
*Assistant Examiner*—Brian M. Bolam
*Attorney, Agent, or Firm*—Richard P. Fennelly; Louis A. Morris

[57] ABSTRACT

Hydrogen bromide can be oxidized to bromine more effectively using hydrogen peroxide as the oxidant if a strong acid (e.g., sulfuric or phosphoric acid) is also present to increase the percent conversion of bromide to bromine.

7 Claims, No Drawings

HYDROGEN PEROXIDE OXIDATION OF BROMIDE TO BROMIDE

This is a continuation of application Ser. No. 474,706 filed Jan. 30, 1990, now abandoned which is a continuation of application Ser. No. 343,713 filed Apr. 27, 1989, now abandoned.

BACKGROUND OF THE INVENTION

1. Field of the Invention

The present invention relates to an improved process for converting bromide (e.g., hydrogen bromide) to bromine using hydrogen peroxide as an oxidant.

2. Description of the Prior Art

In the manufacture of aromatic bromine compounds from an aromatic precursor compound and bromine, about one-half of the bromine value is converted to hydrogen bromide by-product. In order to achieve an economically viable process, the hydrogen bromide has to be oxidized back to bromine. One conventional oxidizing agent which can be used is chlorine. However, use of chlorine has several disadvantages. One major disadvantage is the contamination of the bromine which is produced with chlorine, necessitating use of a purification step before the bromine can be used. Another disadvantage involves the need to dispose of the hydrogen chloride by-product which is formed. The use of hydrogen peroxide as the oxidizing agent would yield water as the by-product and would thus present no purification or disposal problem.

Hydrogen peroxide, however, can act as both an oxidizing and a reducing agent. Unless special techniques are used, it is not possible to obtain high conversions of bromine from hydrogen bromide using hydrogen peroxide as an oxidizing agent.

One limiting case is the oxidation of by-product hydrogen bromide with hydrogen peroxide in the presence of a very reactive aromatic substrate, often a phenol. In this case, as exemplified with the process of Japanese Patent Publication No. 54 39,044, as abstracted in Chem. Abstr. Vol. 91, 91363p, the bromine formed from the oxidation of hydrogen peroxide reacts so fast with the aromatic substrate that no significant amount of bromine is reduced back to hydrogen bromide. However, this is not a general process and would not lend itself, for example, to the polybromination of diphenyl ether.

German Offen. No. 2,713,345 (Chem. Abstr. Vol. 90, 57290g) mentions the addition of aqueous hydrogen peroxide to an aqueous bromide solution, followed by raising of the temperature from room temperature to 35°–45° C. followed by addition of an aqueous alkali bromate. Pure bromine is then distilled from the mixture. The use of sodium bromate, a second oxidizing agent, in such a procedure precludes a full liberation of the bromine values because the sodium bromate is reduced to sodium bromide.

U.S. Pat. No. 4,029,732 solves the problem of removing bromine when hydrogen peroxide is used as an oxidant from bromide ion by physically removing the bromine from the system as rapidly as it is formed by distillation. In the process shown in that patent, the hydrogen bromide can be derived from a bromosulfuric acid solution obtained from the fixation of bromine vapors with sulfur dioxide. Such solutions contain about 0.5 mole of sulfuric acid per mole of hydrogen bromide as a consequence of stoichiometry. This patent, however, stresses (at Col. 1, lines 61–66) that it is necessary to use equipment adapted to effect the separation of bromine substantially as rapidly as it is formed and in effect prevent the bromine from coming into contact with hydrogen peroxide. No mention is made of any favorable result achievable by use of strong acids even though this patent mentions the possible use of a bromosulfuric acid solution reaction medium in one embodiment which is said (at Col. 3, lines 3–7) to contain certain quantities of hydrobromic acid, sulfuric acid, and hydrochloric acid.

More recently, U.S. Pat. No. 4,447,405 teaches that bromide can be removed from arsenic acid solutions by treating such solutions with an oxidant selected from the group consisting of hydrogen peroxide, ozone, or chromium (VI). This patent recognizes that bromine can catalyze the decomposition of hydrogen peroxide and can itself be reduced to bromide by hydrogen peroxide and suggests that the removal efficiency can be improved by preventing the buildup of bromine by the controlled addition of hydrogen peroxide with the simultaneous removal of bromine. It does not suggest that use of a strong acid can improve the bromine conversion percentage in the oxidation of bromide by hydrogen peroxide.

SUMMARY OF THE INVENTION

The invention relates to the oxidation of bromide ions to bromine using hydrogen peroxide as the essential oxidant in the presence of a strong acid which is present in an amount to increase the percent conversion of bromide to bromine.

DETAILED DESCRIPTION OF THE INVENTION

The bromide which is converted to bromine in connection with the present invention is advantageously in the form of hydrogen bromide in aqueous solution and can be present at from about 5% to about 60%, by weight of the solution, preferably 15–30%. As has been mentioned, this hydrogen bromide solution can be derived from a variety of sources, thus making the instant process one of general applicability in the field of organic or inorganic chemistry in providing a suitable means of converting bromide by-product composition to bromine suitable for further reagent use.

The hydrogen peroxide reagent which is added can have a concentration of from about 10% to about 90%, by weight of its (aqueous) solution, preferably 30%–50%. The temperature of treatment of the bromide solution can range from about −15° C. to 59° C., preferably 0° C.–55° C., most preferably 20° C.–55° C.

In accordance with the instant invention, the treatment of bromide with hydrogen peroxide takes place in the presence of an effective amount of a strong acid which acts to improve the conversion percent of bromide to bromine and, hence, the ultimate bromine recovery. The strong acid which is used has a pK of about 3 or below. Representative strong acids include such mineral acids as sulfuric acid, phosphoric acid, and the like. The acid ratio that is used can range from about 0.6 mole to 10 moles of acid per mole of bromide, preferably from about 0.6 mole to 2 moles.

The instant invention is further illustrated by the Examples which follow.

EXAMPLES 1-12

The apparatus used in the Examples which follow consisted of a flask provided with a magnetic stirrer, a subsurface thermometer, an addition funnel, and a condenser over a Barrett moisture trap. The condenser was cooled by means of a circulating refrigerated bath set at 5° C. The flask was sometimes immersed in a cooling bath.

Into the flask was added 48.84% (w/w) hydrogen bromide. When present, 95% sulfuric acid, 85% phosphoric acid, or water were also added. Hydrogen peroxide (30 or 35% w/w) was added at a variable temperature, and then held for a time such that the addition and hold time together totalled four hours. The mixture was then heated at 55° C. for two and one-half hours, followed by distillation of a bromine fraction, usually a water fraction containing some bromine, and a bromine-free water fraction. The bromine fraction was weighed to determine the bromine recovery. The distillation residue was analyzed for hydrogen bromide. This analysis is the basis for the bromine conversion FIGURE. The difference between conversion and recovery is due to mechanical bromine loss and any bromine that might be dissolved in the distilled water.

The "hydrogen bromide concentration" refers to the percent, weight/weight, concentration in the flask after the addition of 48.84% hydrogen bromide, acid, and water.

The data which follows sets forth the particular parameter that was examined (underlined) gives the Example number, and sets forth the variables and the result. Examples 1-5 show that bromine conversion increases in a linear fashion as the amount of acid is increased from 0 to 1.28 moles of hydrogen bromide, but does not increase further with a further increase in acid. Quantitative conversion is possible as illustrated in Examples 11 to 12.

| Effect of Sulfuric Acid | | | | | |
|---|---|---|---|---|---|
| 48.84% Hydrogen bromide, g | | | 141.6 | | |
| Hydrogen bromide concentration, % | | | 16.2 | | |
| 30% Hydrogen peroxide, g | | | 47.7 | | |
| Addition temperature, °C. | | | 2-7 | | |
| Example | 1 | 2 | 3 | 4 | 5 |
| 95% sulfuric acid, | — | 43.4 | 86.8 | 112.8 | 173.6 |
| Water, g | 285.0 | 241.6 | 198.2 | 172.2 | 111.4 |
| Mole H$_2$SO$_4$/mole HBr | — | 0.49 | 0.98 | 1.28 | 1.97 |
| Hydrogen bromide in residue, g | 28.3 | 19.2 | 7.3 | 2.3 | 3.3 |
| Bromine conversion, % | 59.1 | 72.3 | 89.5 | 96.7 | 95.2 |
| Bromine fraction collected, g | 36.7 | 46.8 | 59.0 | 64.3 | 63.7 |
| Bromine recovery, % | 53.7 | 68.4 | 86.3 | 94.0 | 93.1 |
| Effect of Phosphoric Acid | | | | | |
| 48.84% Hydrogen bromide, g | | | 238.2 | | |
| Hydrogen bromide concentration, % | | | 20.0 | | |
| 35% Hydrogen peroxide, g | | | 83.1 | | |
| Addition temperature, °C. | | | 4-8 | | |
| Example | | | 6 | | |
| 85% Phosphoric acid, g | | | 197.2 | | |
| Water, g | | | 211.2 | | |
| Bromine fraction collected, g | | | 100.4 | | |
| Bromine recovery, % | | | 73.5 | | |
| Effect of Temperature | | | | | |
| 48.84% Hydrogen bromide, g | | | 141.6 | | |
| 95% Sulfuric acid, g | | | 86.8 | | |
| Water, g | | | 198.2 | | |
| Hydrogen bromide concentration, % | | | 16.2 | | |
| 30% Hydrogen peroxide, g | | | 47.7 | | |

-continued

| Example | 3 | 7 | 8 |
|---|---|---|---|
| Addition temperature, °C. | 2-9 | 30-40 | 30-55 |
| Hydrogen bromide in residue, g | 7.3 | 6.1 | 6.3 |
| Bromine conversion, % | 89.5 | 91.2 | 90.9 |
| Bromine fraction collected, g | 59.0 | 60.4 | 60.3 |
| Bromine recovery, % | 86.3 | 88.3 | 88.2 |
| Effect of Excess Hydrogen Peroxide | | | |
| 48.84% Hydrogen bromide, g | | 141.6 | |
| 95% Sulfuric acid, g | | 112.8 | |
| Water, g | | 172.2 | |
| Hydrogen bromide concentration, % | | 16.2 | |
| Addition temperature, C | | 2-9 | |
| Example | | 4 | 9 |
| 30% Hydrogen peroxide, g | | 47.7 | 50.1 |
| Hydrogen bromide in residue, g | | 2.3 | 1.5 |
| Bromine conversion, % | | 96.7 | 97.8 |
| Bromine fraction collected, g | | 64.3 | 65.5 |
| Bromine recovery, % | | 94.0 | 95.8 |
| Effect of Hydrogen Bromide Concentration | | | |
| 48.84% Hydrogen bromide, g | | 141.6 | |
| 95% Sulfuric acid, g | | 112.8 | |
| 35% Hydrogen peroxide, g | | 41.4 | |
| Addition temperature, C | | 15-35 | |
| Example | 10 | 11 | 12 |
| Water, g | 172.2 | 91.6 | 0.00 |
| Hydrogen bromide concentration, % | 16.2 | 20.0 | 27.2 |
| Hydrogen bromide in residue, g | 2.9 | 0.4 | 0.1 |
| Bromine conversion, % | 95.8 | 99.4 | 99.9 |
| Bromine fraction collected, g | 65.6 | 66.7 | 66.6 |
| Bromine recovery, % | 95.9 | 97.5 | 97.4 |

The process described and claimed herein can be used in many chemical processes wherein hydrogen bromide is a by-product of a bromination reaction and it is desired to recover the bromine values. A representative process in which the instant technique finds use is in the bromination of diphenyl ether to form pentabromodiphenyl ether in the presence of a suitable catalyst (e.g., an iron catalyst). Such technology is well known (see, for example, U.S. Pat. No. 4,214,103 and the patents cited therein, e g., U.S. Pat. No. 2,022,634).

The foregoing is presented for illustrative purposes only and should not therefore be construed in a limiting sense. The scope of protection sought is set forth in the claims which follow.

I claim:

1. A process for the conversion of bromide ion in solution to bromine comprising the oxidation of bromide ion to bromine by: combining the bromide ion in solution, about 0.6 mole to about 10 moles of a strong acid having a pK$_a$ of about 3 or below per mole of bromide, and an oxidant consisting essentially of from about 10% to about 90% hydrogen peroxide to form a mixture thereof; holding the mixture at a temperature up to about 55° C.; and then distilling a bromine fraction therefrom.

2. A process as claimed in claim 1 wherein the strong acid is selected from the group consisting of sulfuric acid and phosphoric acid.

3. A process as claimed in claim 1 wherein the oxidant is an aqueous solution of 30% to 50% hydrogen peroxide, the strong acid is sulfuric acid, and the acid ratio ranges from about 0.6 mole to about 2 moles of acid per mole of bromide.

4. A process as claimed in claim 3 wherein the strong acid is selected from the group consisting of sulfuric acid and phosphoric acid.

5. A process as claimed in claim 1 wherein the temperature is from 20° C. to 55° C.

6. A process as claimed in claim 3 wherein the temperature is from 20° C. to 55° C.

7. A process as claimed in claim 2 wherein the temperature is from 20° C. to 55° C.

* * * * *